United States Patent [19]

Waller

[11] Patent Number: 4,595,786

[45] Date of Patent: Jun. 17, 1986

[54] HYDRATION OF CYCLOHEXENE IN PRESENCE OF PERFLUOROSULFONIC ACID POLYMER

[75] Inventor: Francis J. Waller, Wilmington, Del.

[73] Assignee: E. I. Du Pont de Nemours and Company, Wilmington, Del.

[21] Appl. No.: 675,429

[22] Filed: Nov. 27, 1984

[51] Int. Cl.$^4$ .............................................. C07C 35/08
[52] U.S. Cl. ................................... 568/835; 568/895; 568/899
[58] Field of Search .................... 568/835, 895, 899

[56] References Cited

U.S. PATENT DOCUMENTS

| | | | |
|---|---|---|---|
| 3,988,379 | 10/1976 | Platz | 568/835 |
| 4,065,512 | 12/1977 | Cares | 568/899 |
| 4,080,391 | 3/1978 | Tsumura et al. | 568/899 |
| 4,306,101 | 12/1981 | Slaugh et al. | 568/835 |
| 4,340,769 | 7/1982 | Brandes et al. | 568/899 |
| 4,358,626 | 11/1982 | Okumura et al. | 568/899 |
| 4,424,388 | 1/1984 | Braithwaite | 568/899 |
| 4,469,905 | 9/1984 | Inwood et al. | 568/835 |
| 4,507,512 | 3/1985 | Okumura et al. | 568/835 |

FOREIGN PATENT DOCUMENTS

| | | | |
|---|---|---|---|
| 686257 | 5/1964 | Canada | 568/835 |
| 8104 | 3/1968 | Japan | 568/835 |
| 26656 | 11/1969 | Japan | 568/835 |
| 918406 | 2/1963 | United Kingdom | 568/899 |
| 2075019 | 11/1981 | United Kingdom | 568/899 |
| 2082178 | 3/1982 | United Kingdom | 568/899 |

*Primary Examiner*—Werren B. Lone
*Attorney, Agent, or Firm*—James A. Costello

[57] ABSTRACT

A catalytic process for the hydration of cyclohexene to cyclohexanol in the presence of perfluorosulfonic acid polymer.

10 Claims, No Drawings

HYDRATION OF CYCLOHEXENE IN PRESENCE OF PERFLUOROSULFONIC ACID POLYMER

BACKGROUND OF THE INVENTION

This invention concerns an improved process for hydrating cyclohexene to cyclohexanol employing perfluorosulfonic acid polymer as the catalyst.

The following publications represent the state of the art for hydrating olefins to alcohols: GB No. 2,082,178A discloses a process for hydrating $C_2$ to $C_6$ olefins in the presence of perfluorosulfonic acid polymer as catalyst. British Pat. No. 918,406 discloses a process for making cyclohexanol from cyclohexene in the presence of a conventional sulfonated polystyrene polymer.

Other publications that disclose olefin hydration include the following: U.S. Pat. No. 4,358,626 (reaction in presence of oxy acid or lactone); U.S. Pat. No. 4,340,769 (sulfonated styrene-divinylbenzene catalyst, $C_2$ to $C_5$ olefin); U.S. Pat. No. 4,065,512 (isobutene); U.S. Pat. No. 4,424,388 (reaction in presence of glycol diether); U.S. Pat. No. 4,080,391 (sulfonic acid catalyst); GB 2,075,019A (methyl t-butyl ether from isobutylene and methanol); and Research Disclosure, 19515, July 1980 (t-butanol from isobutylene and water).

Cyclohexanol is an intermediate in the preparation of adipic acid which is employed principally in the manufacture of nylon. Cyclohexene, the starting reactant of this process, has several interesting characteristics that distinguish its behavior from that of other lower olefins including straight chain olefins such as propylene and the like. For instance, thermodynamic calculations show that hydration of cyclohexene is much less favored than hydration of propylene. It follows, then, that one skilled in the art would expect cyclohexene to be much more difficult to hydrate than propylene and other lower straight chain olefins.

SUMMARY OF THE INVENTION

This invention concerns an improved process for hydrating cyclohexene to cyclohexanol and, more specifically, concerns an improvement in the method disclosed in GB No. 2,082,178A. In a method for hydrating a $C_2$ to $C_6$ olefin to the corresponding alcohol by reacting the olefin with water in the presence of a perfluorosulfonic acid polymer the improvement of this invention consists essentially of employing:

(i) cyclohexene as the olefin reactant in a liquid phase process;
(ii) a reaction temperature of about 175° to 185° C.;
(iii) a water to cyclohexene ratio of about 1:1 to 2.5:1; and
(iv) a hold-up time of about 20 to 30 minutes;

to produce cyclohexanol at a conversion above 4%, and a selectivity above 80%.

For purposes of this invention, hold-up time (HUT) is defined as follows:

$$HUT = \frac{\text{Working Volume of Reactor (mL)} - \text{Volume of Catalyst (mL)}}{\Sigma \text{ Liquid Flow Rates (mL/hr)}} \times 60 \text{ min/hr}$$

wherein a density of 1.0 g/mL is used for the perfluorosulfonic acid polymer catalyst.

Percent Conversion = $10^2 \times$ [mols cyclohexanol + 2(mols cyclohexene dimer)/mols unreacted cyclohexene + mols cyclohexanol + 2(mols cyclohexene dimer)].

Percent Selectivity = $10^2 \times$ [mols cyclohexanol/mols cyclohexanol + 2(mols cyclohexene dimer)].

DETAILS OF THE INVENTION

Perfluorosulfonic acid polymers that can be employed as catalysts typically have number average molecular weights of at least about 5,000. The polymer should contain a sufficient number of sulfonic acid groups to give an equivalent weight of about 500 to 20,000, preferably about 900 to 2,000. Although the polymer backbone will largely comprise perfluorinated carbon atoms, other atoms such as ether oxygen can be present in the backbone or in the side chains of the polymer. Other moieties such as hydrogen, chlorine and carboxyl groups can also be present in limited amounts so long as they do not adversely affect the stability of the polymer under process conditions. It is preferred that the polymer contain no more than about 5 weight percent, based on total weight, of such other atoms or moieties.

The catalyst can be employed in any of a variety of shapes and forms including particles, films, cylindrical modules, supported on a porous support, and the like. It is most conveniently employed in the form of particles that pass through screens in the range of about 20 to 60 mesh. Although a solvent is neither required nor preferred for the hydration reaction, a suitable chemically inert solvent can be employed such as tetramethylenesulfone or the like.

The reaction pressure is not critical. It is determined to a large degree by the molar ratio of water to cyclohexene employed and the relative size of the reaction vessel. Pressures of about 0.5 to 10 MPa are ordinarily employed. The type of reactor used is not critical as long as it is able to withstand the temperatures and pressures involved. Pressure vessels of high tensile steel are typically used, either lined or unlined. Suitable reactor liners include nickel-base corrosion resistant alloys, stainless steel, silver, copper, tantalum, glass and glazed ceramics.

The reaction is conveniently carried out in a stirred reaction vessel with cyclohexene being continuously added to the bottom of the reactor and water continuously added to the top of the reactor. The reactions products are readily separated from water, e.g., by extraction, and cyclohexanol can be conveniently purified by distillation. This process allows easy separation of organics and the insoluble water phase by simple decantation.

Because of the thermal stability and high reactivity of the perfluorosulfonic acid polymer catalysts, cyclohexene hydration can be carried out at higher temperatures with correspondingly shorter reaction times than processes employing sulfonated polystyrene resins as catalysts. Additional details concerning the contemplated polymer catalysts can be found in the literature, including U.S. Pat. No. 3,282,875, U.S. Pat. No. 3,882,093 and U.S. Pat. No. 4,041,090.

With regard to the contemplated method for making cyclohexanol, it will be appreciated by one skilled in the art that a continuous process employing a recycle stream will be the most effective commercial process. In such a process, the relatively high selectivities of above 80% achieved by the process of this invention are significantly more desirable than, say, the 50% selectivities of Comparative Examples A and F (see Table 2) because of the higher ratios of product to by-product that are obtained.

The following Examples illustrate the invention. All parts are by weight, and all degress are Celsius unless otherwise noted.

General Procedure

Hydrations were carried out in a 5-mL nickel alloy (Hastelloy ® C) microreactor configured with a thermocouple, oscillatory agitator, outlet tube for continuous removal of liquid, and two tubes for addition of liquids. Cylcohexene was added to the bottom of the reactor and water was added to the top. The reactor was immersed in a fluidized sand bath for uniform control of temperature.

In a typical procedure of this invention, the reactor was charged with the catalyst and then assembled. The desired olefin flow rate was started, followed by a doubled water flow rate. After 45 minutes, the water flow rate was reduced to the desired level and the reactor pressure, temperature and agitator rate were established at the experimental set points. Samples were collected every hour and analyzed by GC using a 10 ft×⅛ inch (3.05 m×0.32 cm) stainless steel column packed with 10% methylsilicone oil (SE-30) on 80/100 mesh diatomaceous earth. The temperature program for the analysis was 110° (2 min) to 220° at a heating rate of 16°/minute. Helium flow was 34 mL/min. The hydration experiment was usually carried out for 6 to 8 hours.

EXAMPLES 1 TO 3

These experiments were carried out by the General Procedure using a perfluorosulfonic acid polymer catalyst of equivalent weight 1100 as determined by titration of the sulfonic acid groups (Du Pont Nafion ® perfluorosulfonic acid polymer). Reaction pressure was 300 psi (2.1 MPa), and reaction temperature was 180°. The reaction products comprised, in addition to cyclohexanol, various double bond isomers of cyclohexyl-cyclohexene. Results are summarized in Table 1.

TABLE 1

| | Flow mL(mmol)/hr | | | | Sample | | | |
|---|---|---|---|---|---|---|---|---|
| Ex. | $C_6H_{10}$ | $H_2O$ | Mols $H_2O/C_6H_{10}$ | Catalyst g | Time Hr | HUT Min | Conv. % | Selectivity % |
| 1 | 8.0(79) | 2.8(156) | 1.97 | 0.8 | 6 | 23 | 5.5 | 91.5 |
| 2 | 8.0(79) | 2.8(156) | 1.97 | 1.0 | 6 | 22 | 4.8 | 91.5 |
| 3 | 8.0(79) | 1.4(78) | 0.99 | 0.75 | 8 | 27 | 5.2 | 86.0 |

COMPARATIVE EXAMPLES A TO H

These experiments were carried out by the General Procedure employed for Examples of the invention. Primary differences were in the excess of $H_2O$ to cyclohexene employed (Example A), elevated reaction temperatures (Examples B and H); elevated reaction temperature and too low HUT (Examples C and D); too low reaction temperature (Examples E and G); too high HUT (Example F). The results are summarized in Table 2 which demonstrates the interrelated character of process steps (i) to (iv). When steps (i) to (iv) meet the definition of the invention, the cylohexanol is produced at the desired commercial targets for conversion/selectivity; see Table 1. However, when one or more of process steps (i) to (iv) are outside the definition of the invention, either conversion (Example E) or selectivity (Examples A to D and F to H) will be too low.

TABLE 2

| | Flow mL(mmol)/hr | | | | | Sample | | | |
|---|---|---|---|---|---|---|---|---|---|
| Ex. | $C_6H_{10}$ | $H_2O$ | Mols $H_2O/C_6H_{10}$ | Catalyst g | Temp. | Time Hr | HUT Min | Conv. % | Selectivity % |
| A | 5.9(58) | 3.2(178) | 3.07 | 1.0 | 180 | 6 | 26 | 8.6 | 49.6 |
| B | 8.0(79) | 1.4(78) | 0.99 | 0.75 | 210 | 7 | 27 | 52.8 | 1.7 |
| C | 12.0(119) | 4.2(233) | 1.96 | 0.75 | 190 | 7 | 16 | 49.3 | 1.5 |
| D | 18.0(178) | 6.3(350) | 1.97 | 0.75 | 190 | 7 | 11 | 8.6 | 5.5 |
| E | 8.0(79) | 2.8(156) | 1.97 | 0.75 | 160 | 7 | 24 | 0.2 | 100 |
| F | 2.0(20) | 0.7(39) | 1.95 | 1.0 | 180 | 5 | 89 | 11.1 | 50.3 |
| G | 8.0(79) | 2.8(156) | 1.97 | 0.75 | 170 | 6 | 24 | 16.1 | 26.4 |
| H | 8.0(79) | 2.8(156) | 1.97 | 0.75 | 190 | 6 | 24 | 30.1 | 8.2 |

The embodiments of the invention in which an exclusive property or privilege is claimed are defined as follows:

1. In a method for hydrating a $C_2$ to $C_6$ olefin to the corresponding alcohol by reacting the olefin with water in the presence of a perfluorosulfonic acid polymer catalyst, the improvement which consists essentially of employing:

(i) cyclohexene as the olefin reactant in a liquid phase process;

(ii) a reaction temperature of about 175° to 185° C.;

(iii) a water to cylcohexene ratio of about 1:1 to 2.5:1; and (iv) a hold-up time of about 20 to 30 minutes;

the method further characterized by producing cyclohexanol at a conversion above 4% and a selectivity above 80%.

2. A method according to claim 1 employing a perfluorosulfonic acid polymer catalyst having a number average molecular weight of at least 5,000 and an equivalent weight of sulfonic acid groups of about 500 to 20,000, said polymer having no more than about 5 weight percent, based on total weight, of hydrogen, chlorine, ether oxygen or carboxyl moieties.

3. A method according to claim 2 employing the catalyst in the form of particles.

4. A method according to claim 1 run in an inert solvent.

5. A method according to claim 1 run at a pressure of 0.5 to 10 MPa.

6. A method according to claim 2 run at a pressure of 0.5 to 10 MPa.

7. A method according to claim 3 run at a pressure of 0.5 to 10 MPa.

8. A method according to claim 5 run continuously.

9. A method according to claim 6 run continuously.

10. A method according to claim 7 run continuously.

* * * * *